United States Patent [19]

Kato et al.

[11] 4,385,169
[45] May 24, 1983

[54] REACTIVE ALPHA AMINO ACID POLYMER

[75] Inventors: Yoshinori Kato; Hisashi Fukushima, both of Hino; Takeshi Hara, Hachioji, all of Japan

[73] Assignee: Teijin Limited, Osaka, Japan

[21] Appl. No.: 265,924

[22] Filed: May 21, 1981

[30] Foreign Application Priority Data

| May 21, 1980 | [JP] | Japan | 55-66352 |
| Jun. 12, 1980 | [JP] | Japan | 55-78304 |
| Jul. 7, 1980 | [JP] | Japan | 55-91661 |
| Aug. 4, 1980 | [JP] | Japan | 55-106376 |

[51] Int. Cl.$^3$ .................. C08G 69/48; C08G 69/10
[52] U.S. Cl. ......................... 528/321; 525/420; 528/328
[58] Field of Search ............... 528/328, 321; 525/420

[56] References Cited

U.S. PATENT DOCUMENTS 4,046,722 9/1977 Rowland ............................... 260/6

OTHER PUBLICATIONS

Nature, vol. 255 pp. 487-488 (1975).
Lancet, pp. 1105-1106 (1977).
Proc. Natl. Acad. Sci., U.S.A. vol. 79, pp. 621-625 (1982).

*Primary Examiner*—Harold D. Anderson
*Attorney, Agent, or Firm*—Sughrue, Mion, Zinn, Macpeak and Seas

[57] ABSTRACT

A reactive polymer having the degree of polymerization in the range of 5 to 3,000, with 60 mole % or more of the whole constituent units comprising the constituent units expressed by formula (I)

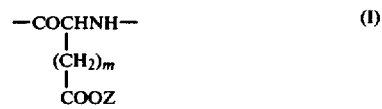

wherein Z indicates a hydrogen atom or a univalent cation; m is an integer 1 to 4:

and has an active group expressed by formula (II) at the carboxyl end of the main chain

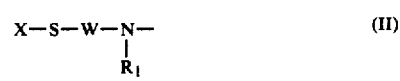

wherein X indicates a hydrogen atom or a group which can form an active disulfide linkage together with a neighboring sulfur atom; W is a divalent organic group; and $R_1$ represents a hydrogen atom or an alkyl group having 1 to 4 carbon atoms.

Since this reactive polymer can bind to cytotoxic substances, which contain an amino group or imino group in the molecule by way of the carboxyl group of the side chain and it also can bind to, for instance, antitumor immunoglobulins by way of an active group (thiol group or active disulfide group) at the end of the main chain, it can be used as a polymer carrier in the preparation of target seeking antitumor drugs.

4 Claims, No Drawings

REACTIVE ALPHA AMINO ACID POLYMER

BACKGROUND OF THE INVENTION

1. Field of the Invention

The present invention relates to a highly reactive polymer, which has a good number of carboxyl groups (or their salts) on its side chains and at the same time has a thiol group or an active group containing an activated disulfide linkage at one end of its main chain and a process for the preparation thereof. And it is an object of the present invention to provide a polymer to be used for the linking of an antitumor antibody and cytotoxic substances in the making of a target seeking anti-cancer drug (antitumor drug) which is prepared by linking said antitumor antibody, which is capable of linking with a target tumor cell, and said cytotoxic substances, which work as anti-cancer drugs.

2. Description of the Prior Art

It has hitherto been publicly known to use a reactive polymer as a medium with the object of increasing efficiency in linking an antitumor antibody and a cytotoxic substance in the preparation of a target seeking anti-cancer drug.

For instance, U.S. Pat. No. 4,046,722 (G. D. Searle & Co. Limited) issued on Sept. 6, 1977, discloses an antitumor drug which comprises an antitumor immunoglobulin and a polymer carrier, for instance, polyglutamic acid, having 5–500 molecules of a cytotoxic drug covalently bonded thereto, bonded by amide linkages. The antitumor drug obtained in this way is a very interesting chemotheraputics in that it is expected to be selectively directed to the tumor target to exert its toxic action within the tumor cell.

However, a demerit of this publicly known antitumor drug is that the linkage of this antitumor antibody and the cytotoxic part (the polymer carrier linked with an anticancer drug) is effected by amide linkages, more particularly the linkages are effected by means of free amino groups or carboxyl groups contained in the antitumor antibody. An immunoglobulin molecule has many amino groups or carboxyl groups at its antigen seeking subunit. Therefore, in an attempt to conjugate a cytotoxic substance to an antitumor immunoglobulin by means of an amide linkage, the antigen seeking subunit of the antitumor immunoglobulin also becomes conjugated with the cytotoxic substance, thus lowering its function of seeking the antigen. As a result, this poses a problem of making the obtained antitumor drug totally or partially lose its function to bind to the tumor cell. Also the method provided in U.S. Pat. No. 4,046,722 allows the formation of amide linkages in the antibody molecules and polyglutamic acid molecules, or between the same kinds of molecules. The formation of such an undesirable amide linkage results in the decreased efficacy of the obtained antitumor drug and further raises a problem to cause by-production of a high molecular weight polymer substance which is unsuited for a use for treatment of tumor patients.

SUMMARY OF THE INVENTION

As a result of an earnest research work to overcome such demerits as found in the prior art, the present inventors have found that an antitumor drug which is free from said demerit can be obtained by directly conjugating a thiol group (or an S-sulfo group) which is obtained by cleaving the disulfide linkage existing in a specific part of an immunoglobulin, with a cytotoxin, or by conjugating a modified immunoglobulin, which is prepared by chemically introducing thiol groups or any groups that can be linked with thiol groups into the immunoglobulin beforehand, with a cytotoxic substance. The present invention provides a reactive polymer which can be used most satisfactorily for the preparation of such an antitumor drug as mentioned above or other target seeking drugs.

The present invention relates to a reactive polymer having the degree of polymerization in the range of 5 to 3000, with 60 mole % or more, preferably 80 mole % or more of the whole constituent units comprising the constituent unit expressed by formula (I)

wherein Z indicates a hydrogen atom or a univalent cation; m is an integer 1 to 4:
and has an active group expressed by formula (II) at the carboxyl end of the main chain

wherein X indicates a hydrogen atom or a group which can form an active disulfide linkage together with a neighboring sulfur atom; W is a divalent organic group; $R_1$ represents a hydrogen atom or an alkyl group having 1 to 4 carbon atoms.

Of the above reactive polymers, a polymer (or a reactive polymer having a terminal thiol group) in which said X is a hydrogen atom can be obtained by reductively cleaving the disulfide linkage of a hydrophilic polymer, which has the degree of polymerization in the range of 5 to 3,000, with 60 mole % or more, preferably 80 mole % or more, of its whole constituent units comprising the constituent unit expressed by formula (I) and has a disulfide linkage containing group expressed by formula (III) in the main chain or at the carboxyl end of the main chain

wherein W and $R_1$ has the same meaning as defined in the case of said formula (II); $R_2$ indicates an alkyl group, aralkyl group, or aryl group when the group expressed by formula (III) is the end group of the main chain, and indicates a divalent group expressed by

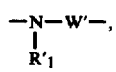

when the group expressed by formula (III) is in the main chain,
wherein W' is a divalent organic group identical with or different from W and is linked with S of formula (III); $R_1'$ is identical with or different from $R_1$ and represents a hydrogen atom or an alkyl group having 1 to 4 carbon atoms.

A polymer, in which X is a group capable of forming an active disulfide linkage together with a neighboring sulfur atom, can be obtained by reacting the reactive polymer, which has a terminal thiol group (—SH) and is obtained as in the above, with a reactive disulfide compound.

The reactive polymer of the present invention is to provide a reactive polymer, which is conjugated with cytotoxic substances, has the degree of polymerization in the range of 5 to 3,000, and contains an active group expressed by said formula (II) at the carboxyl end of the main chain, by allowing said reactive polymer itself to react with a cytotoxic substance which contains an amino group or imino group in its molecule, so that 60 mole % or more, preferably 80 mole % or more of the whole constituent units may consist of a mixture of a constituent unit expressed by said formula (I) and a constituent unit expressed by formula (IV)

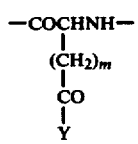

(IV)

wherein Y indicates a reaction residue of the amino group or imino group of the cytotoxic substance which contains an amino group or imino group in its molecule; and m is an integer 1 to 4.

Such a reactive polymer conjugated with a cytotoxic substance can also be obtained by allowing a hydrophilic polymer, with 60 mole % or more, preferably 80 mole % or more of its whole constituent units comprising the constituent unit expressed by said formula (I), having a disulfide containing group expressed by said formula (III) in the main chain or at the carboxyl end of the main chain, to react with a cytotoxic substance which contains an amino group or imino group in its molecule, then by reductively cleaving the disulfide linkage of the reaction product or by changing the thiol group resulting from such cleavage into an active disulfide linkage.

DESCRIPTION OF THE PREFERRED EMBODIMENTS

The reactive polymer of the present invention can be conjugated with such a cytotoxic substance as an anticancer drug, etc. by means of many carboxyl groups (or their salts) on its side chains and also can be conjugated with an immunoglobulin of antitumor antibody, etc. by means of an active group at the end of its main chain.

In formula (I), Z is a hydrogen atom or a monovalent cation, for instance, $Na^+$, $K^+$ and $NH_4^+$. m indicates an integer 1 to 4 but a preferable result is obtained when m is 1 or 2. Of the constituent units expressed by formula (I) in the reactive polymer of the present invention, those in which m=1 and those in which m=2 may exist together and the reactive polymer functions satisfactorily so far as the total of those constituent units is 60 mole % or more, preferably 80 mole % or more of the whole constituent units.

The reactive polymer of the present invention may contain any constituent units other than those expressed by formula (I) within the range of less than 40 mole % of the whole constituent units. To adduce examples, there are such α-amino acids as glycine, alanine, phenylalanine, cerin, etc. that have no carboxyl group (or its salt) on the side chain at the α-position.

The constituent unit consisting of such α-amino acid takes no part in conjugated the polymer with a cytotoxic substance; however, it may be of some use in adjusting the water-solubility of the reactive polymer itself and also in adjusting the water- and fat-solubility of the polymer conjugated with a cytotoxic substance. Therefore, in cases where the adjustment of fat- and water-solubility is not specifically required, it is better not to let the polymer contain the constituent units consisting of such α-amino acid from the practical point of view.

In formula (II), X represents a hydrogen atom or a group which can form an active disulfide linkage together with a neighboring sulfur atom. As for the latter, there are, for instance,

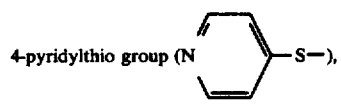

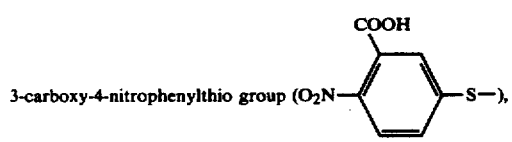

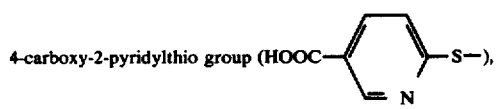

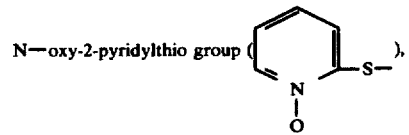

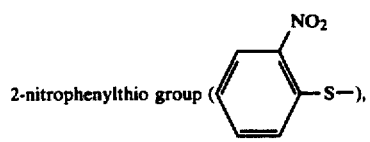

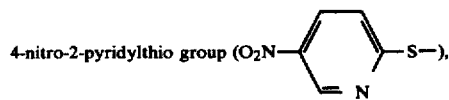

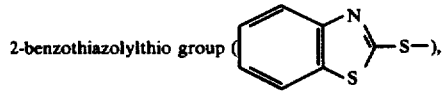

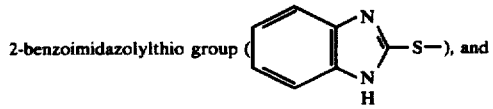

N—phenylamino-N'—phenyliminomethylthio group

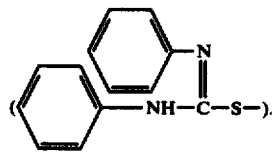

In formula (II), W indicates a divalent organic group and no limit is set to its kind so far as it is an inactive group that virtually exerts no influence on the reaction during the process in which the reactive polymer of the present invention is prepared and in the succeeding reaction processes. As for these groups, there are, for instance, alkylene groups such as straight-chain 2-aminoethanethiol residue ($-CH_2CH_2-$) or side-chain cysteinebenzylester residue

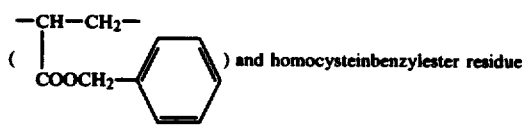

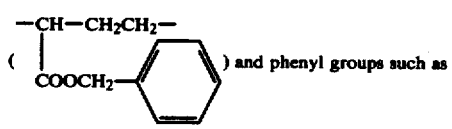

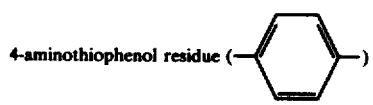

having no substituent or having a substituent; however, an alkylene group having 1 to 4 carbon atoms is especially preferable. $R_1$ is a hydrogen atom or an alkyl group having 1 to 4 carbon atoms; however, a hydrogen atom is more preferable.

An explanation shall hereunder be made on the method of preparing a reactive polymer of the present invention in which X is a hydrogen atom or one which has an active group expressed by the following formula (II-a) at the carboxyl terminal of the main chain $$HS-W-N- \atop R_1 \qquad (II\text{-}a)$$

wherein W and $R_1$ respectively have the meaning defined for formula (II).

It is a method in which a hydrophilic polymer, 60 mole % or more of which constituent units comprises the constituent units expressed by said formula (I) and which has a group containing a disulfide linkage expressed by the following formula (III) in the main chain or at the carboxyl terminal of the main chain is made to react with a thiol compound or boron hydride compound to reductively cleave the disulfide linkage contained in the polymer:

wherein W and $R_1$ respectively have the meaning defined the formula (II); $R_2$ indicates an alkyl group, aralkyl group, or aryl group, when the group expressed by formula (III) is an end group of the main chain, and indicates a divalent group represented by $$-N-W'- \atop R'_1 \text{,}$$

when the group expressed by formula (III) is in the main chain; in which W' is a divalent organic group identical with or different from W and is linked with S of formula (III); $R'_1$ is identical with or different from $R_1$ and represents a hydrogen atom or an alkyl group having 1 to 4 carbon atoms. The reaction of the hydrophilic polymer with the thiol compound is usually conducted in a homogeneous reaction system in which water or an organic solvent such as dimethylformamide, dimethyl sulfoxide, etc. is used as a reaction solvent. Suitable thiol compounds are, for instance, dithiothreitol and 2-mercaptoethanol. Thiol compounds are used 1 to 100 times the molar quantity of the disulfide linkages contained in the polymer. The reaction temperature should preferably be in the range of $-5°$ C. to $70°$ C. and the reaction time be 5 minutes to 10 days.

In the case where a boron hydride compound, for instance, sodium borohydride, potassium borohydride, etc., is used, its reaction with the polymer is usually carried out in an aqueous solution.

An explanation shall next be made on the method of preparing a reactive polymer of the present invention in which X is a group which can form a disulfide linkage together with a neighboring sulfur atom or one which has an active group expressed by the following formula (II-b) at the carboxyl terminal of the main chain

wherein W and $R_1$ respectively have the meaning defined for formula (II); X' represents a group which can form an active disulfide linkage together with a neighboring sulfur atom.

It is a method in which a polymer containing an active group expressed by said formula (II-a) at the carboxyl terminal of the molecule obtained as mentioned above, or a polymer containing a thiol group is made to react with an active disulfide compound. Active disulfide compounds include, for instance,

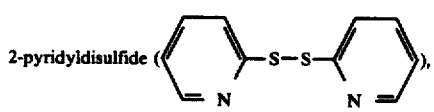

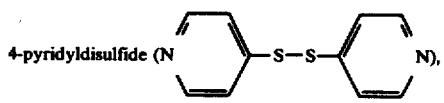

5,5'-dithio-bis(2-nitrobenzoic acid)

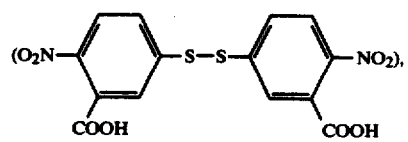

-continued 4-carboxy-2-pyridyldisulfide

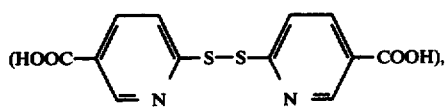

N—oxy-2-pyridyldisulfide
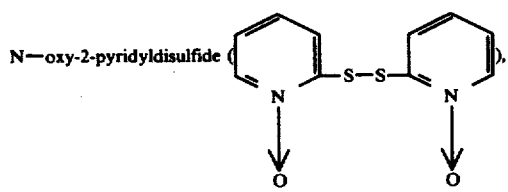

2-nitrophenyldisulfide
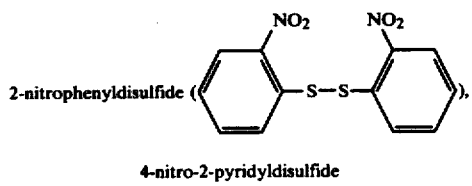

4-nitro-2-pyridyldisulfide
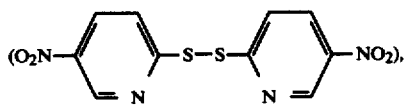

2-benzothiazolyldisulfide
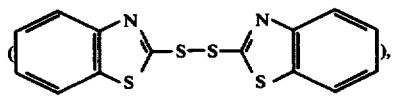

2-benzoimidazolyldisulfide
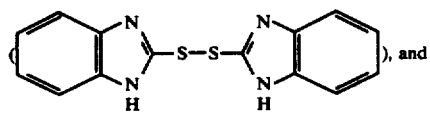

N—phenylamino-N'—phenyliminomethyldisulfide
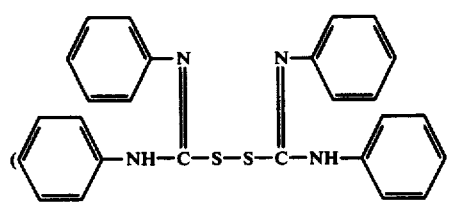

The abovementioned reaction between them is usually conducted in a homogeneous reaction system in which water or an organic solvent such as dimethylformamide, dimethyl sulfoxide, etc. is used as a reaction solvent. The reaction can also be carried out in a reaction system comprising an admixture of an aqueous solution of the polymer, an active disulfide compound or its acetone solution or its dioxane solution. It is proper to conduct the reaction at −5° to 70° C. for 1 minute to 24 hours.

An explanation shall be made on the hydrophilic polymer—an intermediate in the preparation of said reactive polymer—which has a disulfide linkage containing a group expressed by said formula (III) in the main chain or at the carboxyl terminal of the main chain.

In the abovementioned formula (III), $R_1$ and $R'_1$ are either a hydrogen atom or an alkyl group having 1 to 4 carbon atoms; however, a hydrogen atom is more preferable. $R_2$ is an alkyl group, aralkyl group, or aryl group, when the group expressed by formula (III) is an end group of the main chain. In this case, the hydrophilic polymer of the present invention can be represented as follows (provided that the constituent units of formula (I) is 100 mole %):

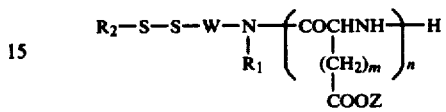

wherein n indicates the number of the constituent units; $R_2$ is a divalent group expressed by

when the group expressed by formula (III) is in the main chain. In this case, the hydrophilic polymer of the present invention can be represented as follows (provided that the constituent units of formula (I) is 100 mole %):

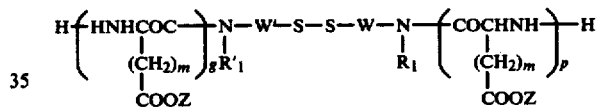

wherein p and q respectively indicate the number of the constituent units.

The reactive polymer and the hydrophilic polymer of the present invention should have the degree of polymerization in the range of 5 to 3000, preferably 10 to 1500. When the degree of polymerization is less than 5, the amount of cytotoxic substances to couple with the polymer is too small to make an efficient reactive polymer in the preparation of antitumor drugs. If the degree of polymerization exceeds 3000, it not only makes the preparation process difficult but also makes the handling inconvenient in the preparation of antitumor drugs.

The aforementioned hydrophilic polymer can be prepared according to the method mentioned below. It is a method in which a polymer, 60 mole % or more, preferably 80 mole % or more of whose constituent units comprises the constituent units expressed by the undermentioned formula (V)

wherein X is a carboxyl-protecting group, representing an alkyl group having 1 to 4 carbon atoms, benzyl group, and benzyl substituent; and m is an integer 1 to 4: the polymer having a disulfide linkage containing group expressed by the aforementioned formula (III) in the main chain or at the carboxyl terminal of the main chain, and having the degree of polymerization in the range of 5 to 3000, is decomposed with acid or alkali to remove the carboxyl-protecting group X; or further followed by the formation of a salt with the regenerated carboxyl group and a univalent cation, as case may require.

As for the carboxyl-protecting group X, a lower alkyl group having 1 to 4 carbon atoms, benzyl groups, and a substituted benzyl group are preferably used, of which a methyl group and benzyl group are especially preferable.

The decomposition reaction by use of acid to eliminate the carboxyl-protecting group X is desirable, for instance, in the case where X is a lower alkyl group, or benzyl group, or a substituted benzyl group. Acids to be used in the acid decomposition reaction are, for instance, hydrochloric acid, hydrobromic acid, trifluoroaceti acid, and methanesulfonic acid. Preferable reaction solvents are, for example, water, formic acid, acetic acid, and trifluoroacetic acid, and acid may also serve as a solvent.

The reaction temperature differs depending upon the kind of acid to be used and in the case of water-hydrobromic acid system, it is proper to conduct the reaction at 90° to 100° C., and in the case of hydrobromic acid-trifluoroacetic acid at 0° to 30° C. The proper reaction time is in the range of 30 minutes to 100 hours. The reaction may be carried out either in the stream of nitrogen or by addition of anisole or the like to the reaction system so that side reactions may be suppressed.

After the reaction is over, the acid and solvent are partly removed by distillation under decreased pressure and a nonreactive organic solvent such as ether, etc. is added to the residue to obtain the hydrophilic polymer of the present invention as a precipitate.

The hydrophilic polymer thus obtained is, if required, made to react with an alkali such as lithium hydroxide, sodium hydroxide, potassium hydroxide, ammonium hydroxide, sodium carbonate, potassium carbonate, sodium hydrogencarbonate, etc. to form a salt of its carboxyl group and a monovalent cation. The formation of a salt is effected by stirring the admixture, which consists of an aqueous solution or suspension of the hydrophilic polymer and said alkali 1 to 10 times equivalent weight of the carboxyl group, at room or warmed or cooled temperature. Thereafter, the reaction solution is thoroughly dialyzed against, for instance, water and then water is distilled from the dialyzate to obtain the desired hydrophilic polymer (carboxylate).

The alkali decomposition, which is conducted to cleave the protecting group X from the carboxyl group, is desirably adopted when X is a lower alkyl group. Alkalis to be used in the alkali decomposition include, for instance, alkali hydroxide such as lithium hydroxide, sodium hydroxide, potassium hydroxide, etc. or metal alcoholate such as sodium methylate, sodium ethylate, etc. It is advisable to use water, alcohols, dioxane, pyridine, methylene chloride or their mixture as a reaction solvent. The polymer is made to react with the above-mentioned alkali in a state of homogeneous solution or suspension of said solvent. The quantity of alkali to be used may be 1 to 10 moles to 1 mole of ester group; however, in order to suppress the side reaction to cleave the peptide linkage of the main chain of polyglutamic acid, it is advisable to use about 1 to 3 moles.

The suitable reaction temperature is 0° to 50° C. and 5° to 35° C. is especially preferable. The reaction time is usually in the range of 1 hour to 5 days, preferably in the range of 5 hours to 2 days.

After the reaction is completed, the hydrophilic polymer of the present invention is obtained in the form of precipitate when the reaction mixture is neutralized by addition of acid.

Though the method of preparing a polymer which has the aforementioned constituent units (III) and (V) in the molecule is explained in detail in the example given later, its outline is indicated hereunder. For instance, phosgen is made to re-act on glutamic acid benzyl ester (γ-benzyl-L-glutamic acid) to obtain γ-benzyl-L-glutamate N-carboxylic acid anhydride, which is then polymerized by n-propyl 2-aminoethyl disulfide ($CH_3CH_2CH_2S-SCH_2CH_2NH_2$) to give a polymer which has a disulfide linkage containing group at one end of the main chain. When said anhydride is polymerized by, for instance, cystamine ($H_2NCH_2CH_2SSCH_2CH_2NH_2$), a polymer having a disulfide linkage containing group in the main chain is obtained.

The reaction of the reactive polymer of the present invention with a cytotoxic substance which contains an amino group or imino group in the molecule gives a reactive polymer linked to a cytotoxic substance, with 60 mole % or more of the whole constituent units of the polymer consisting of the total of the constituent units expressed by said formula (I) and the constituent units expressed by said formula (IV), having an active group expressed by said formula (II) at the carboxyl terminal of the main chain, and having the degree of polymerization in the range of 5 to 3000.

What is referred to as a cytotoxic substance in the present invention is one which directly exerts cytotoxic action on the tumor cells, or one which does not exert cytotoxic action on cells directly but is convertible in vivo into a substance which exerts cytotoxic action on cells. These cytotoxic substances are:

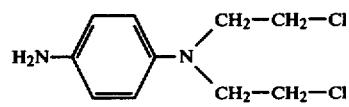

P—[N,N—bis(2-chloroethyl)]phenylenediamine,

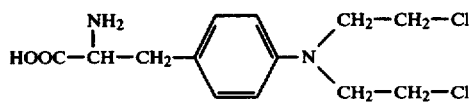

P—[bis(2-chloroethyl)amino]L-phenylalanine(melphalan),

-continued
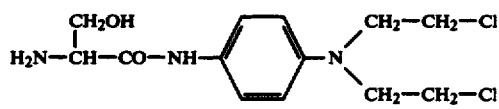
2-mino-N—[P-bis(2-chloroethyl)amino]phenyl-3-hydroxypropionamide,
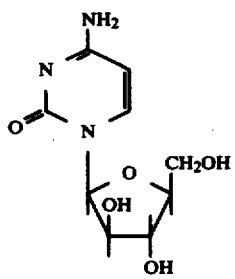
1-(β-D-arabinofuranosyl) cytosine or its monophosphate,
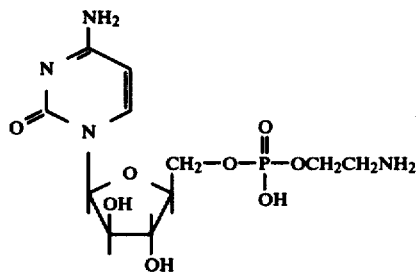
1-[5′-(2-aminoethylphosphoryl)-β-D-arabinofuranosyl]cytosine,
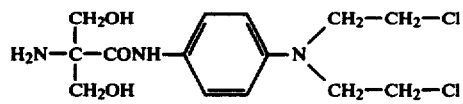
2-amino-N—[P—bis(2-chloroethyl)amino]phenyl-3-hydroxy-2-hydroxymethylpropionamido,
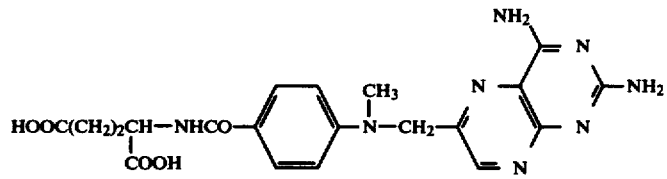
methotrexate,

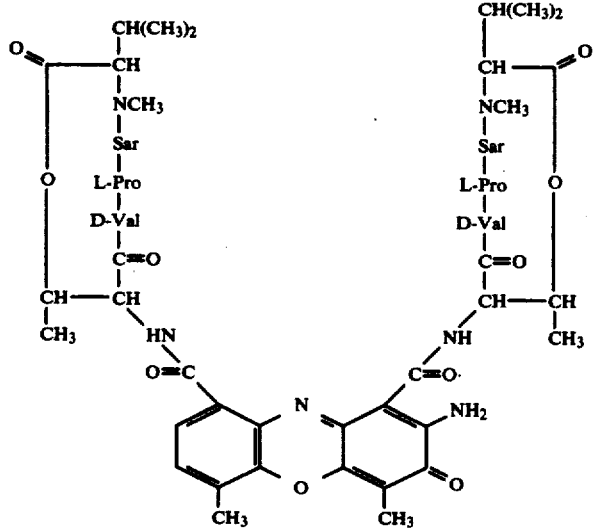

actinomycin D,

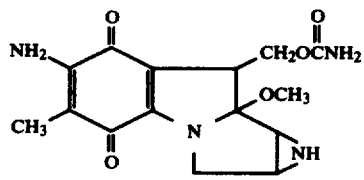

mitomycin,

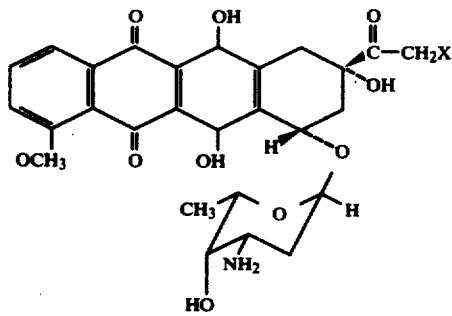

X=H, daunomycin
X=OH, adriamycin.

In the present invention, the reaction of a reactive polymer, which has 60 mole % or more of the constituent units expressed by formula (I) in the molecule and contains an active group expressed by formula (II) at the carboxyl terminal of the main chain, with a cytotoxic substance, which contains an amino group or imino group in the molecule, is usually carried out in a homogeneous reaction system in which water or an organic solvent such as dimethylformamide and dimethyl sulfoxide is used as a reaction solvent. In the reaction, the carboxyl group contained in the polymer may be activated by, for instance, 1-ethyl-3-(3-dimethylaminopropyl) carbodiimide hydrochloride or dicyclohexyl carbodiimide, or the carboxyl group may be activated in the form of a mixed acid anhydride. The reaction may be conducted at −40° to 100° C. for 10 minutes to 10 days. It is advisable to fix the ratio between the polymer and the cytotoxic substance in the reaction in such a way as to have a cytotoxic substance corresponding to 5 to 200% of —COOZ group contained in the polymer.

Also such a reactive polymer coupled to a cytotoxic substance can be obtained by allowing a hydrophilic polymer, or an intermediate in the process of preparing the reactive polymer, which has 60 mole % or more of its whole constituent units consisted of the constituent units expressed by said formula (I) and has a disulfide linkage containing group expressed by said formula (III) in the main chain or at the carboxyl terminal of the main chain, to react with a cytotoxic substance, which contains an amino group or an imino group in the molecule under the same reaction conditions as mentioned above. The first of such methods is one in which the hydrophilic polymer is made to react with the cytotoxic substance, the reaction product is further made to react with a thiol compound or boron hydride compound, and then the disulfide linkage in the reaction product thus obtained is cleaved off by reduction. This process gives a polymer which has an active group (thiol group) expressed by the aforementioned formula (II-a) at the carboxyl terminal of the main chain. The reaction to cleave the disulfide linkage by use of thiol compound is usually conducted in a homogeneous reaction system in which water or an organic solvent such as dimethylformamide and dimethyl sulfoxide is used as a reaction solvent. Suitable thiol compounds include, for instance, dithiothreitol and 2-mercaptoethanol. The thiol compound is used 1 to 100 times the disulfide linkage of the polymer in molar quantity. It is desirable to conduct the reaction at −5° to 70° C. for 5 minutes to 10 days. In the case where a boron hydride compound, such as sodium borohydride, potassium borohydride, and calcium borohydride, is used, the reaction with the polymer is usually conducted in an aqueous solution thereof.

The second of the methods is one in which the polymer that is obtained according to the first method and has a thiol group at the carboxyl terminal of the main chain, is made to react with an active disulfide compound. The active disulfide compounds and the reaction conditions are as same as those which are adopted in the case where the reactive polymer of the present invention is obtained. By this method, the polymer having an active group (active disulfide group) expressed by said formula (II-b) at the carboxyl terminal of the main chain is prepared.

Since the reactive polymer coupled to a cytotoxic substance obtained in the present invention has a highly active thiol group or an active disulfide linkage in the molecule, the reactivity of such group or linkage and the reactivity of a thiol group, active disulfide group, or S-sulfo group contained in the antitumor immunoglobulin are profitably employed to have them both linked together, thus providing an anti-tumor drug which has a toxic subunit (cytotoxic substance) comprising a reactive polymer linked to a cytotoxic substance of the present invention.

Some of the embodied methods of preparing such antitumor drugs are given below:

(1) An antitumor immunoglobulin is treated with pepsin to give a dimer of Fab'. The disulfide linkage at the hinge part of this dimer of Fab' is cleaved reductively by use of, for instance, a thiol reagent to obtain Fab' which has a thiol group in the molecule. Fab' having a thiol group thus obtained is made to react with the reactive polymer of the present invention having an active disulfide linkage to obtain the desired antitumor drug.

(2) The disulfide linkage at the hinge part of said dimer of Fab' is decomposed by sulfonation with the use of, for instance, sulfite ion to obtain Fab' which has an S-sulfo group (—S—SO₃−) in the molecule. The obtained Fab' having an S-sulfo group is then made to react with the reactive polymer of the present invention having a thiol group to give the desired antitumor drug.

(3) A functional group which is able to react with a thiol group is introduced into an antitumor immunoglobulin beforehand. Then this modified immunoglobulin is allowed to react with the reactive polymer of the present invention having a thiol group to obtain the desired antitumor drug. Embodiments include the following instance:

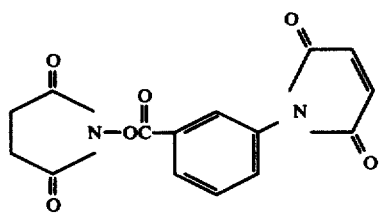

is made to bind to an amino group of the immunoglobulin. Then a terminal thiol group of the reactive polymer of the present invention is allowed to react with thus introduced maleoyl group to obtain the desired antitumor drug.

The antitumor drug thus prepared is expected to bind to tumor cells selectively and exert toxic action against tumor cells.

The reactive polymer bound to a cytotoxic substance of the present invention can also be utilized for preparing a targetable drug which destroy the lymphocyte, when it is bound to such an antibody other than antitumor antibody as an antilymphocyte antibody.

The following examples are presented to further illustrate the present invention.

EXAMPLE 1

(1) Preparation of γ-benzyl-L-glutamate-N-carboxylic acid anhydride:

A dispersion was prepared by adding 10.0 g of ι-benzyl-L-glutamic acid to 120 ml of tetrahydrofuran anhydride. Apart from this, phosgene was generated by dropping 20 ml of trichloromethyl chloroformate little by little onto 10.0 g of carbon black in an atmosphere of nitrogen for the duration of 70 minutes. Generated phosgene was sent into the dispersion of γ-benzyl-L-glutamic acid in an atmosphere of nitrogen. After 70 minutes the dispersion turned to a pale yellow-colored transparent solution and the introduction of phosgene was stopped. After that, nitrogen was sent into the system to eliminate phosgene. The solvent was removed from the obtained transparent solution by distillation in a stream of nitrogen under reduced pressure (140 mm Hg, 27° C.).

The residue was dissolved in 150 ml of n-hexane. The solution was then stirred on an ice bath for 5 minutes to give a white solid precipitate. This solid substance was refined by being precipitated twice in the system of ethyl acetate-n-hexane (anhydrous) in an atmosphere of nitrogen. The refined substance was then filtered with suction and dried under reduced pressure to give 7.75 g of γ-benzyl-L-glutamate N-carboxylic acid anhydride (having the following structural formula) as a white solid

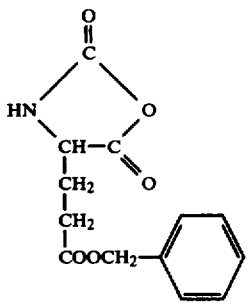

This had a melting point of 94.0° to 94.5° C. (decomposition) and its yield was 69.8%.

(2) Preparation of poly-L-glutamate (hydrophilic polymer):

7.75 g of γ-benzyl-L-glutamate N-carboxylic acid anhydride was dissolved in 185 ml of 1,4-dioxane with stirring in an atmosphere of nitrogen. An admixture, which consists of thus obtained solution and a solution prepared by dissolving 95 mg of cystamine ($H_2NCH_2CH_2SSCH_2CH_2NH_2$) in 10 ml of dioxane, was subjected to the polymerizing reaction at room temperature in an atmosphere of nitrogen with stirring for 24 hours. After the reaction was over, the reaction mixture was added to 4 l of isopropyl ether while stirring and the formed polymer was allowed to precipitate. The precipitated white polymer was collected by filtration and dried under reduced pressure to give 6.19 g of the desired polymer in a 95.9% yield.

The average molecular weight of the obtained polymer measured by the viscosity method (dichloroacetic acid, 25.0° C.) was 47,300 (Refer to P. Doty et al, Journal of Americal Chemical Society, Vol. 78, p. 947, 1956). It was reasonably presumed from the starting material, initiator and reaction mechanism that it mainly comprised poly-γ-benzyl-L-glutamate represented by the formula mentioned below. It was also confirmed by infrared absorption spectrum.

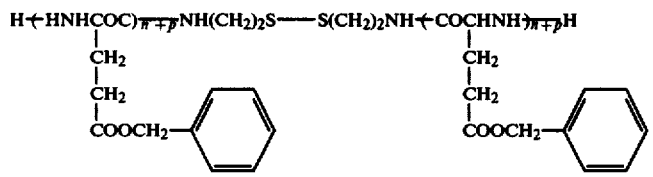

(Molecular weight: 47,300
n + p + n' + p' = 216)

3.11 g of poly-γ-benzyl-l-glutamate obtained in the above was dissolved in a mixture of 25.0 ml of trifluoroacetic acid and 4.5 ml of anisole. 25.0 ml of methanesulfonic acid was then added to thus prepared solution and was stirred in an atmosphere of nitrogen on an ice bath for 20 minutes. The solution was further stirred at room temperature for 30 minutes to carry out the acid decomposition reaction of γ-benzyl ester. After the reaction was over, the reaction mixture was added to 450 ml of isopropyl ether with stirring to make the polymer precipitate. The precipitated white polymer was collected by filtration with suction and suspended in 50 ml of water. About 60 ml of saturated aqueous solution of sodium bicarbonate was added to the suspension to conduct the neutralization reaction of the carboxyl group at room temperature with stirring for 30 minutes. The obtained reaction solution was dialyzed against pure water at 4° C. for 3 days on a cellulose tube and was then lyophilized to give 1.91 g of white solid substance. When the obtained solid was examined by infrared absorption spectrum, it was confirmed that there was no absorption of benzyl ester and that the carboxyl group was turned into the sodium salt. The yield of poly-L-glutamate as the sodium salt was 9.3%.

Its average molecular weight measured according to the viscosity method (solution of common salt in phosphoric acid buffer; ionic strength, 0.11 and 1.10; 25.5° C.) was 29,200 (Refer to R. B. Hawkins et al, Macromolecules, Vol. 5, p. 294, 1972). The obtained polymer mainly comprises the sodium salt of poly-L-glutamate represented by the following formula

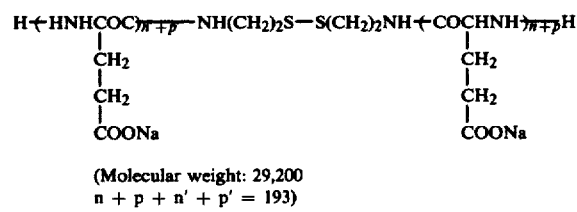

(Molecular weight: 29,200
n + p + n' + p' = 193)

The above shows a hydrophilic polymer in which m=2 and Z=Na+ in formula (I) and W=W'=—(CH₂)₂— and R₁=R₁'=H in formula (III).

EXAMPLE 2

5.50 g of γ-benzyl-L-glutamate N-carboxylic acid anhydride obtained in Example 1, (1) was dissolved in 150 ml of 1,4-dioxane in an atmosphere of nitrogen with stirring. A solution obtained by dissolving 142 mg of n-propyl 2-aminoethyldisulfide ($CH_3CH_2CH_2SSCH_2CH_2NH_2$) in 10 ml of dioxane was added to the abovementioned solution. The mixed solution was then subjected to the polymerization reaction in an atmosphere of nitrogen at room temperature for 40 hours with stirring. After the reaction was over, the reaction mixture was added to 4 l of isopropyl ether with stirring and the formed polymer was precipitated. The precipitate was collected by filtration and dried under reduced pressure to give 4.41 g of the desired polymer in a 96.3% yield.

4.00 g of the obtained polymer was then dissolved in a mixture consisting of 35 ml of trifluoroacetic acid and 5.0 ml of anisole. 35 ml of methanesulfonic acid was added to the solution and the mixture was stirred in an atmosphere, firstly while being cooled with ice for 30 minutes and then at room temperature for another 30 minutes to carry out the acid decomposition of γ-benzyl ester. After the reaction was over, the reaction mixture was added to 540 ml of isopropyl ether with stirring to precipitate the polymer. The polymer was then collected by filtration. The collected polymer was dissolved in 100 ml of a 5% aqueous solution of sodium bicarbonate to neutralize the carboxyl group. The reaction solution was dialyzed against pure water at 4° C. for 3 days on a cellulose tube. When the obtained solution was lyophilized 2.33 g of sodium poly-L-glutamate (yield 77.4%) was obtained as a hygroscopic curdy solid. It was found from infrared absorption spectrum inspection of the obtained polymer that there was no absorption of benzyl ester and that the carboxyl group was turned into the sodium salt. The average molecular weight measured according to the same method as mentioned above was 16,700. The obtained polymer consists mainly of the sodium salt of poly-L-glutamate represented by the following formula

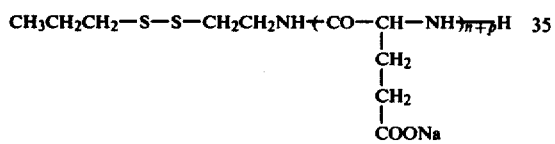

(Molecular weight: 16,700
n + p = 110)

This shows a hydrophilic polymer in which m=2 and Z=Na+ in formula (I) and W=—(CH$_2$)$_2$—, R$_1$=H$_1$ and R$_2$=—(CH$_2$)$_2$CH$_3$ in formula (III).

EXAMPLE 3

10.0 g of γ-benzyl-L-glutamate N-carboxylic acid anhydride obtained according to Example 1, (1) and 0.23 g of L-alanine N-carboxylic acid anhydride were put in 280 ml of 1,4-dioxane in an atmosphere of nitrogen and stirred to have them dissolved. A solution prepared by dissolving 198 mg of 4-aminophenyl disulfide in 10 ml of dioxane was added to the solution obtained in the above and was mixed. The mixture was stirred in an atmosphere of nitrogen at room temperature for 24 hours to carry out the polymerization reaction. After the reaction was over, the reaction mixture was put in 4 l of isopropyl ether while stirring to obtain a polymer as a precipitate. The precipitated polymer was filtered off and dried under reduced pressure to give 8.21 g of the polymer. The yield was 97%. It was reasonably presumed from the starting material, initiator and reaction mechanism that the obtained polymer was an undermentioned copolymer of γ-benzyl-L-glutamate and L-alanine. This was also confirmed by infrared absorption spectrum.

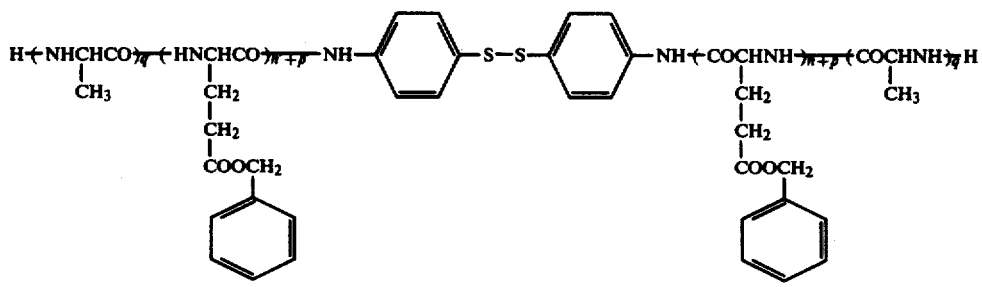

4.0 g of thus obtained copolymer was dissolved in a mixture of 30 ml of trifluoroacetic acid and 5.0 ml of anisole. 30 ml of methanesulfonic acid was added to the prepared solution and stirred on an ice bath for 20 minutes. The stirring was further continued at room temperature for 30 minutes to carry out the acid decomposition of γ-benzyl ester. After the reaction is over, the reaction mixture was added to 600 ml of isopropyl ether with stirring to precipitate a polymer. The precipitated white polymer was filtered off with suction and was then suspended in 65 ml of water. About 80 ml of water saturated with sodium bicarbonate was added thereto and mixed. The mixture was stirred at room temperature for 30 minutes to effect the neutralization of the carboxyl group to make a homogeneous solution. The obtained solution was dialyzed at 4° C. for 3 days against pure water on a cellulose tube and then lyophilized to give 2.45 g of a white solid. When this solid was examined by infrared absorption spectrum, it was confirmed that there was no absorption of benzyl ester and that the carboxyl group was turned to sodium salt. The yield of polymer as the sodium salt was 88%. The obtained polymer consists mainly of the sodium salt of the polymer of L-glutamate and L-alanine expressed by the following formula

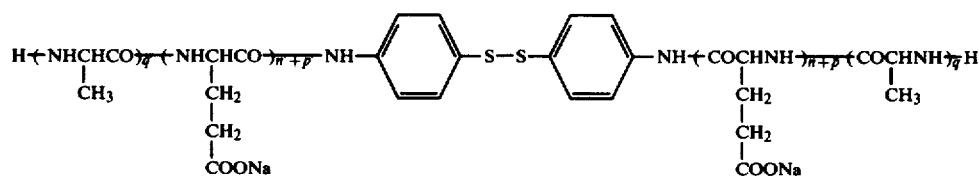

This shows a hydrophilic polymer in which m=2 and Z=Na+ in formula (I) and

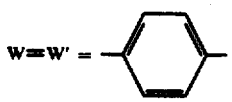

W=W' = and $R_1 = R_1' = H$ in formula (III).

EXAMPLE 4

This example shows an instance from several methods of preparing a reactive polymer which has a thiol group at the terminal of the molecule.

292 mg (10μ mole) of sodium salt of poly-L-glutamate having a disulfide linkage in the main chain obtained in Example 1, (2) was dissolved in 10 ml of 0.1 M tris.hydrochloric acid-1 mM EDTA solution (pH 8.50), to which 78 mg (1 m mole) of 2-mercaptoethanol was added. The obtained solution was heated and stirred in an atmosphere of nitrogen at 50° C. for 3 hours (whereby the disulfide linkage was cleaved). The reaction solution was then titrated to pH 2.0 with 1 N hydrochloric acid and the resulting precipitate was separated by centrifugation. The precipitate was dissolved in about 25 ml of 0.1 N caustic soda solution, to which 1 N hydrochloric acid was added to adjust the pH to 7.0. A dispersion prepared by dispersing 30 ml in wet volume of activated thiopropyl sepharose 6B resin in 40 ml of 0.1 M sodium phosphate-1 mM EDTA solution (pH 7.0) was added to the above solution. The mixture was stirred slowly in an atmosphere of nitrogen for 12 hours to make the polymer, which has an SH group at the terminal of the molecule, to be held by adsorption on the resin. The resin was then filterred off and washed with 300 ml of 0.01 M sodium phosphate-1 mM EDTA solution (pH 7.0).

Thereafter, the resin was dispersed in 100 ml of 0.1 M tris-hydrochloric acid-1 mM EDTA solution (pH 8.5). 1.4 g of 2-mercaptoethanol was added to the dispersion and the mixture was stirred slowly in an atmosphere of nitrogen for 12 hours to regenerate a polymer having an SH group at the terminal of the molecule. Then the resin was collected by filtration and washed with 150 ml of 0.01 M tris.hydrochloric acid-1 mM EDTA solution (pH 8.0). A mixture of the filtrate and the washings was titrated to pH 2 with 1 N hydrochloric acid on an ice bath and the obtained precipitate was isolated by centrifugation.

The precipitate thus obtained is a reactive polymer which has a thiol group at the terminal of the molecule. This is the reactive polymer in which Z=Na+ and m=2 in formula (I) and W=—(CH₂)₂— and $R_1 = H$ in formula (II-a).

EXAMPLE 5

(1) Preparation of a reactive polymer having an active disulfide linkage at the terminal of the molecule The reactive polymer having a thiol group at the terminal of the molecule obtained in the Example 4 was dissolved in about 25 ml of 0.1 N caustic soda solution, to which 1 N hydrochloric acid was added to adjust the pH value of 8.0. A solution prepared by dissolving 79 mg of 5,5'-dithio-bis(2-nitrobenzoic acid) (DTNB) in 5 ml of 0.1 M sodium phosphate-1 mM EDTA solution was added to the above solution and the mixture was stirred for 30 minutes (whereby the SH group at the terminal of the molecule formed an active disulfide linkage).

The obtained reaction solution was placed in a permeable cellophane tube to be dialyzed against 0.9% saline solution at 4° C. for 24 hours and further against pure water for 24 hours. Thereafter, the dialyzate was lyophilized to give 181 mg of the desired sodium salt of polyglutamic acid (reactive polymer) in the form of a curdy solid having the terminal of the molecule activated with TNB

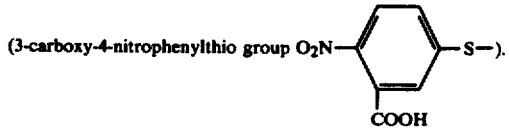

(3-carboxy-4-nitrophenylthio group O₂N— —S—).

COOH

The yield was 62%

(2) Determination of molecular weight of a reactive polymer having an active disulfide linkage at the terminal of the molecule 10.02 mg of the reactive polymer obtained in the preceding (1) was weighed accurately and dissolved in 3.0 ml of 0.1 M tris.hydrochloric acid-1 mM EDTA solution (pH 8.0), to which about 0.1 mg of solid dithiothreitol was added and stirred. Ten minutes later, the quantity of the end groups of the reactive polymer was determined by measuring the absorption intensity of the liberated TNB anions at 412 nm to be 0.794μ mole. Therefore, the molecular weight of the obtained reactive polymer is $$\frac{10.02 \times 10^{-3}}{0.794 \times 10^{-6}} \approx 12,600$$

and the number of units of the constituent glutamic acid is $12,600/151 \approx 83$.

EXAMPLE 6

This example shows an instance of method for preparing a reactive polymer having a thiol group at the terminal of the molecule.

100 mg (6.00μ mole) of sodium salt of poly-L-glutamate having a disulfide linkage containing group at the carboxyl terminal of the main chain was dissolved in 5 ml of 0.1 M tris.hydrochloric acid-1 mM EDTA solution (pH 8.0), to which 9.24 mg (60μ mole) of dithiothreitol was added. The obtained solution was stirred in an atmosphere of nitrogen at 50° C. for 3 hours. Then the pH value of the solution was lowered to 2.0 by adding 1 N hydrochloric acid while cooling with ice and the settled precipitate was isolated by centrifugation. The obtained precipitate was dissolved in about 10 ml of 0.1 N NaOH, to which 1 N hydrochloric acid was added to raise the pH to 7.0. A dispersion prepared by dispersing 9 ml in wet volume of activated thiopropyl sepharose 6B resin in 12 ml of 0.1 M sodium phosphate-1 mM EDTA solution (pH 7.0) was added to the solution prepared above. The mixture was stirred in an atmosphere of nitrogen for 12 hours. Then the resin was filtrated off and washed with 200 ml of 0.01 M sodium phosphate-1 mM EDTA solution (pH 7.0).

The resin was dispersed in 50 ml of 0.1 M tris.hydrochloric acid-1 mM EDTA solution (pH 8.5), to which 139 mg of dithiothreitol was added. The mixture was stirred slowly in an atmosphere of nitrogen for 12 hours. Thereafter, the resin was filtrated off and washed with 70 ml of 0.01 M tris.hydrochloric acid- 1 mM EDTA solution (pH 8.0). The filtrate and the washings were mixed, to which 1 N hydrochloric acid was added to lower the pH to 2.0 and the developed precipitate was isolated by centrifugation.

The obtained precipitate is a reactive polymer which has a thiol group at the terminal of the molecule.

EXAMPLE 7

(1) Preparation of a reactive polymer having an active disulfide linkage at the terminal of the molecule The precipitate obtained in Example 6 was dissolved in 10 ml of 0.1 N caustic soda solution, to which 1 N hydrochloric acid was added to adjust the pH to 7.0. A solution prepared by dissolving 26.4 mg of 2-pyridyldisulfide in 4 ml of ethanol to the above solution and was stirred for 30 minutes. The obtained reaction solution was placed in a permeable cellophane tube and dialyzed at 4° C. against 30% ethanol for 24 hours and against pure water for another 24 hours. Then the dialyzate was freeze-dried to give 56 mg of the desired sodium salt of polyglutamic acid (reactive polymer) in the form of a curdy solid having the terminal of the molecule activated with 2-pyridylthis group

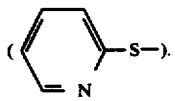

The yield was 56%.

(2) Determination of molecular weight of a reactive polymer having an active disulfide linkage at the terminal of the molecule 9.53 mg of the reactive polymer obtained in the preceding (1) was weighed accurately and dissolved in 3.00 ml of 0.1 M sodium phosphate-1 mM EDTA solution (pH 7.0), to which about 0.1 mg of solid dithiothreitol was added and stirred. Ten minutes later, the quantity of the end groups of the reactive polymer was determined by measuring the absorption intensity of the liberated 2-pyridylthio anions at 343 nm to be $0.561\mu$ mole.

Therefore, the molecular weight of the obtained reactive polymer is $$\frac{9.53 \times 10^{-3}}{0.561 \times 10^{-6}} \approx 17,000$$

and the number of units of the constituent glutamic acid is $$17,000/151 \approx 113.$$

EXAMPLE 8

This example shows an instance of method for preparing a reactive polymer having a thiol group at the terminal of the molecule.

100 mg of hydrophilic polymer (a sodium salt of the copolymer of L-glutamic acid and L-alanine) having a disulfide linkage in the main chain was dissolved in 5 ml of 0.1 M tris.hydrochloric acid-1 mM EDTA solution (pH 8.5). 10.0 mg of dithiothreitol was added thereto and the obtained solution was stirred in a heating bath at 50° C. for 3 hours in an atmosphere of nitrogen. The reaction solution then had its pH lowered to 2.0 by adding 1 N hydrochloric acid while cooling with ice. The developed precipitate was isolated by centrifugation. The obtained precipitate was dissolved in 10.0 ml of 0.1 N sodium carbonate solution and the pH was raised to 7.0 by adding 1 N hydrochloric acid thereto. A dispersion prepared by dispersing 10 ml in wet volume of activated thiopropyl sepharose 6B resin in 13 ml of 0.1 M sodium phosphate-1 mM EDTA solution (pH 7.0) was added to the above solution and was stirred in an atmosphere of nitrogen for 12 hours. The resin was then filtrated off and was washed with 200 ml of 0.01 M sodium phosphate-1 mM EDTA solution (pH 7.0).

Thereafter, the resin was dispersed in 50 ml of 0.1 M tris.hydrochloric acid-1 mM EDTA solution (pH 8.5), to which 150 mg of dithiothreitol was added, and was stirred slowly in an atmosphere of nitrogen for 12 hours. The resin was then collected by filtration and washed with 100 ml of 0.01 M tris.hydrochloric acid-1 mM EDTA solution (pH 8.0). The mixture of the filtrate and the washings had its pH lowered to 2.0 by adding 1 N hydrochloric acid on an ice bath. The developed precipitate was isolated by centrifugation.

The obtained precipitate is a reactive polymer which has a thiol group at the terminal of the molecule.

EXAMPLE 9

(1) Preparation of a reactive polymer having an active disulfide linkage at the terminal of the molecule The precipitate obtained in Example 8 was dissolved in 10 ml of 0.1 N caustic soda solution and the pH value of the solution was adjusted to 7.7 by adding 1 N hydrochloric acid. A solution prepared by dissolving 17 mg of 5,5'-dithio-bis(2-nitrobenzoic acid) (DTNB) in 20 ml of acetone was added thereto and the mixture was stirred for 30 minutes. The obtained reaction solution was placed in a permeable cellophane tube and was dialyzed against 0.9% saline solution at 4° C. for 24 hours and against pure water for another 24 hours. The dialyzate was then lyophilized to give 51 mg of the desired sodium salt of a copolymer of L-glutamic acid and L-alanine (reactive polymer) in the form of a curdy solid having the terminal of the molecule activated with TNB. The yield was 51%.

(2) Determination of molecular weight of a reactive polymer having an active disulfide linkage at the terminal of the molecule The reactive polymer obtained in the preceding (1) was weighed 10.16 mg accurately and dissolved in 3.0 ml of 0.1 M sodium phosphate-1 mM EDTA solution (pH 7.0), to which about 0.1 mg of solid dithiothreitol was added and stirred. Ten minutes later, the quantity of the end groups of the reactive polymer was determined to be $1.026\mu$ mole of measuring the absorption intensity of the liberated TNB anions at 412 nm. Therefore, the molecular weight of the obtained reactive polymer is $$\frac{10.16 \times 10^{-3}}{1.026 \times 10^{-6}} \approx 9,900$$

and since the ratio of the glutamic acid units and alanine units is 95:5, the respective constituent units are $$\frac{9,900}{151 \times 0.95 + 71 \times 0.05} \times 0.95 = 64 \text{ and}$$

$$\frac{9,900}{151 \times 0.95 + 71 \times 0.05} \times 0.05 = 3.4$$

EXAMPLE 10

(1) Preparation of a reactive polymer bound with mitomycin C 50 mg of the reactive polymer (molecular weight, 12,600, number of units of glutamic acid, 83) having a 3-carboxy-4-nitrophenyl-2-aminoethyldisulfide residue prepared in Example 5, (1) and 55.5 mg (0.166 m mole) of mitomycin C were dissolved in 10 ml of 0.1 M sodium phosphate buffer (pH 7.0). 126 mg of 1-ethyl-3-(3-dimethylaminopropyl)carbodiimide was dissolved in the above solution and was stirred at room temperature overnight. Then 54 mg of sodium acetate was added to the reaction system and was stirred for half an hour to complete the reaction. The reaction solution was fractionated by chromatography on Sephadex G-25 (fine) column (1.4×80 cm) in 0.02 M sodium phosphate to obtain 7.5 ml-fractions. Each fraction had its absorbance measured at 360 nm to detect those fractions containing the reactive polymer-mitomycin C conjugates. The corresponding fractions were combined and was dialyzed against water at 4° C. for 2 days. The dialyzate was distilled under reduced pressure to have its volume reduced to 3.0 ml, to which 1.0 ml of 0.1 M sodium phosphate-1 mM EDTA solution (pH 7.0) was added to make a total of 4.0 ml.

50.0 μl of this obtained solution of the reaction polymer-mitomycin C conjugates (The object matter of the present invention) was added to 2.0 ml of a buffer (pH 8.0) and its UV absorption spectrum was measured. The absorption max arising from the residue of mitomycin C was observed at 360 nm to assure that the object matter of the present invention was formed.

(2) Determination of mitomycin C in the reaction polymer-mitomycin C conjugate

The quantity of mitomycin C residue contained in the solution (4.0 ml) of the reactive polymer-mitomycin C conjugate obtained in the preceding (1) was 0.081 m mole when determined by conveniently setting the molecular absorbancy index of the mitomycin C residue at $\epsilon$ 360 nm=23,000 (Refer to J. S. Webb et al., the J.A.C.S., Vol. 84, p. 3185, 1962).

On the other hand, the number of moles of the reactive polymer was determined to be 2.69μ moles from the quantity of the end groups of the reactive polymer measured from the absorption max (412 nm, $\epsilon$=13,600) of the 5-thio-2-nitrobenzoic acid anions which were generated by adding a large excess of dithiothreitol to a certain amount of solution of the reactive polymer-mitomycin C conjugate. Therefore, the number of mitomycin C bound to one molecule of the reactive polymer is calculated to be 0.081×10$^{-3}$/2.69×10$^{-6}$=30.1.

EXAMPLE 11

(1) Preparation of a reactive polymer linked with 5'-(2-aminoethylphosphoryl)-1-(β-arabinofuranosyl) cytosine (Ara CMP derivative)

22.8 mg of 1-ethyl-3-(3-dimethylaminopropyl)carbodiimide hydrochloric acid salt was dissolved in a mixture consisting of a solution obtained by dissolving 6.04 mg of the reaction polymer (molecular weight, 17,000; glutamic acid units, about 113) having the 2-pyridyl 2-aminoethyldisulfide residue at the terminal of the molecule obtained in the aforementioned Example 7 in 1.0 ml of 0.1 M sodium phosphate buffer (pH 7.5) and a solution obtained by dissolving 7.16 mg of 5'-(2-aminoethylphosphoryl)-1-(β-D-arabinofuranosyl) cytosine (hereinafter referred to as Ara CMP derivative) in 1.0 ml of the same buffer. The mixed solution stirred at room temperature for 12 hours. Then 9.84 mg (0.12 m mole) of sodium acetate was added to the reaction system and was further stirred for half an hour to complete the reaction. The obtained reaction solution was column chromatographed by Sephadex G-25 (fine) having a bed volume of 41.6 ml in 0.05 M sodium phosphate-1 mM EDTA solution (pH 6.9) and the eluate was collected in 3 ml-fractions. Each fraction had its absorbance determined at 273 nm to detect the fractions which contained reactive polymer-Ara CMP derivative conjugate, which fractions were then collected and put in in a permeable cellophane tube to be dialyzed against pure water at 4° C. for 48 hours. The dialyzate was concentrated to 1.5 ml by distillation under reduced pressure, to which 0.5 ml of 0.1 M sodium phosphate-1 mM EDTA solution to give a total of 2.0 ml.

50.0 μl of thus obtained solution of the reactive polymer-Ara CMP conjugate (the object matter of the present invention) was added to 2.0 ml of water. When the ultraviolet absorption spectrum was measured with this mixture, the maximal absorption due to the cytosine group of, the Ara CMP was observed at 273 nm and it was confirmed that the object matter of the present invention was formed.

(2) Determination of Ara CMP contained in the reactive polymer-Ara CMP derivative conjugate:

The quantity of the Ara CMP residues contained in the solution (2.0 ml) of the reactive polymer-Ara CMP conjugate obtained in the preceding (1) was 9.79μ modes when determined by conveniently setting the molecular absorbancy index of the Ara CMP residue at $\epsilon$ 273 nm=9,000 (Refer to The Merck Index, 9th ed., p. 2778).

The number of moles of the reactive polymer was determined to be 0.291μ mole from the quantity of the end groups of the reactive polymer measured from the maximal absorption (343 nm, $\epsilon$=7,000) of 2-thiopyridone resulting from the addition of a large excess of dithiothreitol to a certain amount of solution of the reactive polymer-Ara CMP conjugate.

From the above value, the number of Ara CMP to one molecule of the reactive polymer is accordingly is calculated to be 9.79×10$^{-6}$/0.291×10$^{-6}$=33.6.

EXAMPLE 12

(1) Preparation of a reactive polymer linked with P-[N,N'-bis(2-chloroethyl)] phenylendiamine (PDM)

100 mg of the reactive polymer (molecular weight, 9,900; glutamic acid units, 64; alanine units, 3.4) having 3-carboxy-4-nitrophenyl 4-aminophenyldisulfide residue at the terminal of the molecule obtained in the aforementioned Example 9, (1) was dissolved in 3 ml of water, in which 14.8 mg of 1-ethyl-3-(3-dimethylaminopropyl)carbodiimide hydrochloric acid salt was dissolved. Then a solution prepared by dissolving 17.4 mg of PDM hydrochloric acid salt in 3 ml of water was added thereto. After the reaction solution was stirred for 1 hour, the pH was adjusted to 3.5 with 1.0 N HCl. The developed white precipitate was filtrated off and washed with 0.001 N HCl. The obtained precipitate was dissolved in 5 ml of 0.1 N NaOH solution, put in a permeable cellophane tube, and dialyzed against water at 4° C. for 2 days. Then the dialyzate was lyophilized to give 111.0 mg of desired curdy solid of the reactive polymer-PDM conjugate.

5.46 mg of thus obtained reactive polymer-PDM conjugate was weighed accurately and dissolved in 10.0 ml of 0.05 M tris-HCl solution (pH 8.0). When its ultraviolet absorption spectrum was measured, the maximal absorption due to the PDM residue was observed at 275 nm and it was confirmed that the object matter of the present invention was formed.

(2) Determination of PDM in the reactive polymer-PDM conjugate

The quantity of the PDM residues contained in 111.0 mg of the reactive polymer-PDM conjugate obtained in the preceding (1) was 60.2μ moles when determined by conveniently setting the molecular absorbancy index of the PDM residue at $\epsilon 275$ nm=16,200 (the absorbance of acetylated PDM was used).

The number of moles of the reactive polymer was determined to be 9.81μ moles from the quantity of the end groups of the reactive polymer measured from the maximal absorption (412 nm, $\epsilon=13,600$) of 5-thio-2-nitrobenzoic acid anions resulting from the addition of a large excess of dithiothreitol to a solution of a certain amount of the reactive polymer-PDM conjugate. Accordingly, the number of PDM bound to one molecule of the reactive polymer is calculated to be $60.2\times 10^{-6}/9.81\times 10^{-6}=6.1$.

EXAMPLE 13

(1) Preparation of a reactive polymer linked with 1-(β-D-arabinofuranosyl) cytosine:

200 mg of the reactive polymer (Na salt) (molecular weight, 12,600; glutamic acid unit, 83) having the 3-carboxy-4-nitrophenyl 2-aminoethyldisulfide residues obtained in Example 5 was dissolved in 4.0 ml of water. The solution had its pH adjusted to 4.0 by adding 1 N HCl dropwise on an ice-bath. The developed precipitate was filtered off, washed with 0.001 N hydrochloric acid, and dried under vacuum to give 151 mg of a white solid by poly-L-glutamic acid.

100 mg of thus obtained reactive polymer having free carboxylic acid was dissolved in 10 ml of dimethylformamide. After the solution was cooled to −7° C., 106 mg of isobutyl chloroformate and 78 mg of triethylamine and was added thereto and stirred for 1 hour to make the carboxyl groups of poly-L-glutamic acid into the form of a mixed acid anhydride. Then a solution prepared by dissolving 188 mg of 1-(β-D-arabinofuranosyl) cytosine in 10 ml of dimethylformamide was added to the reaction liquid, to which 78 mg of triethylamine was further added. The reaction was conducted in an atmosphere of nitrogen at −7° C. for 30 minutes, at 0° C. for 4 hours, at 4° C. for 3 days and at room temperature for 4 hours to allow poly-L-glutamic acid to link with Ara C. After the reaction was completed, the reaction solution was added to 30 ml of 1 N-sodium phosphate buffer (pH 8.0) on an ice bath. The mixed solution was dialyzed on a cellophane membrane at 4° C. against 3% salt solution for 2 days and against pure water for another 2 days. The volume of the dialyzate was reduced to about 10 ml by distillation under reduced pressure. The dialyzate was then freeze-dried to have the solvent removed and 145 mg of a reactive polymer linked with Ara C was obtained in the form of a curdy solid.

1.12 mg of thus obtained reactive polymer-Ara C conjugate was weighed accurately and dissolved in 5.00 ml of 0.1 M tris-HCl-1 mM EDTA solution (pH 8.0). When its ultraviolet absorption spectrum was measured, the absorption max was observed at 300 nm, 247 nm and 216 nm, from which it was made clear that the $N^4$-position (amino group of Ara C formed the amid linkage with the carboxyl group of the glutamic acid unit (Refer to M. Akiyama et al., Chem. Pharm. Bull., Vol. 26, p. 981, 1978).

(2) Determination of Ara C in the reactive polymer Ara C conjugate:

The quantity of the Ara C residues contained in 145 mg of the above conjugate was 145μ moles when determined by conveniently setting the molecular absorbancy index of the maximal absorption at 300 nm as 8,000 (Refer to the literature mentioned in the preceding paragraph). Then the number of moles of the reactive polymer was determined to be 6.61μ moles from the quantity of the end groups contained in the reactive polymer calculated from the maximal absorption (412 nm, $\epsilon=13,600$) of 5-thio-2-nitrobenzoic acid anions liberated by reductively cleaving the terminal active disulfide by addition of a large excess of dithiothreitol to a solution of a certain amount of the conjugate. Accordingly, the number of Ara C bound to one molecule of the reactive polymer is calculated to be $145\times 10^{-6}/6.61\times 10^{-6}=21.9$.

EXAMPLE 14

(1) Preparation of a reactive polymer linked with daunomycin:

A reactive polymer (molecular weight, 17,000; glutamic acid units, 113) having a 4-pyridyl 2-aminoethyldisulfide residue at the terminal of the molecule was obtained from the reactive polymer, which was obtained in Example 6, having a thiol group at the terminal of the molecule, according to the same method as Example 7 with the exception of the use of 4-pyridyldisulfide as an active disulfide compound in place of 2-pyridyldisulfide.

50 mg of the freeze-dried reactive polymer thus obtained was dissolved in 10 ml of water, in which 475 mg of 1-ethyl-3-(3-dimethylaminopropyl)carbodiimide hydrochloric acid salt was dissolved. A solution, prepared by dissolving 63 mg of daunomycin hydrochloric acid salt in 10 ml of water, and 10 ml of DMF were added thereto. The mixture was allowed to react at room temperature overnight. Thereafter, 200 mg of sodium acetate was added and the reaction was completed.

After the reaction is over, 10 ml of 0.5 M sodium phosphate buffer (pH 8.0) was added to the reaction liquid on an ice bath. The obtained solution was dialyzed at 4° C. on a cellophane membrane against 0.1 M sodium phosphate-0.5 M NaCl (pH 8.0) for 2 days and against pure water for another 2 days. After insoluble substances in the dialyzate were removed by centrifugation, the volume of the solution was reduced to 10 ml by distillation under reduced pressure. Then the solvent was removed from the solution by freeze-drying to give 70.5 mg of a reactive polymer linked with daunomycin as a red curdy solid.

Accurately weighed 1.59 mg of thus obtained reactive polymer-daunomycin conjugate was dissolved in 1.00 ml of 0.1 M sodium phosphate buffer (pH 8.0). When its ultraviolet absorption spectrum was measured, the maximal absorption was observed at 535 nm (sh), 490 nm, 289 nm (sh) and 252 nm (sh), from which it was confirmed that that object matter of the present invention was produced (Refer to E. M. Acton et al., J. Med. Chem., Vol. 17, p. 659, 1974).

(2) Determination of daunomycin in the reactive polymer-daunomycin conjugate:

The quantity of the daunomycin residue contained in 70.5 mg of the abovementioned conjugates was 43.7μ mole when determined by conveniently setting the molecular absorbancy index of the maximal absorption at 490 nm at $1.2 \times 10^4$ (refer to the abovementioned literature). Then the number of moles of the reactive polymer was determined to be 2.68μ moles from the quantity of the end groups contained in the reactive polymer calculated from the maximal absorption (324 nm, $\epsilon = 1.98 \times 10^4$) of 4-thiopyridone liberated by reductively cleaving the terminal active disulfide by addition of a large excess of dithiothreitol to a solution of a certain amount of the conjugate (in measuring the absorbance at 324 nm, the calculation was made by use of a value from which the absorption of light by daunomycin residues was deducted). Accordingly, the number of daunomycin bound to one molecule of the reactive polymer is calculated to be $43.7 \times 10^{-6}/268 \times 10^{-6} = 16.3$.

EXAMPLE 15

(1) Preparation of poly-L-glutamic acid sodium salt-PDM conjugate:

A solution prepared by dissolving 151.3 mg of 1-ethyl-3-(3-dimethylaminopropyl) carbodiimide hydrochloric acid salt in 5 ml of water was added to a solution prepared by dissolving 475 mg of the polymer, which was obtained in the aforementioned Example 1, (2), mainly comprising the sodium salt of poly-L-glytamic acid. An aqueous solution obtained by dissolving 178.4 mg of p-[N,N-bis(2-chloroethyl)] phenylenediamine hydrochloric acid salt (PDM), which is publicly known as an anti-cancer drug, in 10 ml of water was added thereto dropwise in 7 minutes. The reaction liquid was stirred at room temperature for 30 minutes. When the pH of the reaction liquid was adjusted to 4.0 by adding hydrochloric acid, a white precipitate developed. The precipitate was filtrated off and washed with diluted hydrochloric acid. The obtained white solid was then dissolved in 20 ml of an aqueous solution of 0.1 N caustic soda and dialyzed against pure water at 4° C. on a permeable cellophane tube for 3 days. When the dialyzate was lyophilized, 569.2 mg of a curdy solid (poly-L-glutamate sodium-PDM conjugate) was obtained.

(2) Determination of PDM in the poly-L-glutamate sodium-PDM conjugate:

4.075 mg of the poly-L-glutamate sodium-PDM conjugate obtained in the preceding (1) was dissolved in 100 ml of an aqueous solution containing 10% ethanol and the absorption (275 nm) of the PDM was measured. The found value of the absorbance (275 nm) was 0.730.

Concentration of the PDM residues is calculated according to the following equation:

$$C = \frac{A}{\epsilon \cdot l} = \frac{0.730}{1.62 \times 10^{-4} \times 1.0} = 4.51 \times 10^{-5} \text{ (moles)} \quad (a)$$

(wherein A is a found value of the absorbance, l is 1.0 cm, and $\epsilon$ indicates an absorbancy index, $1.62 \times 10^4$; incidentally, the absorbance of a condensation product of acetic acid and PDM (acetylated PDM) was used as a value of $\epsilon$ for convenience sake.)

On the other hand, when the ratio of L-glutamate-PDM conjugate units to L-glutamate sodium units, from which L-glutamate-PDM conjugate units arose, is represented by a symbol X, the molecular weight M of the L-glutamate unit contained in the polymer is expressed by $M = 151(1-X) + 344X$. Therefore, the molar concentration C of the PDM residue is calculated by the following equation:

$$C = \frac{\text{Weight of the polymer used in the determination (G)}}{M} \times X \times \frac{1000}{100} = \quad (b)$$

$$\frac{4.075 \times 10^{-3}}{151(1-X) + 344X} \times X \times \frac{1000}{100}$$

When the value of X is calculated from the abovementioned equation (a) and equation (b), $X = 0.212$, which leads to a conclusion that 21.2% of the sodium L-glutamate units is turned to the L-glutamate-PDM conjugate units.

Also, the average molecular weight MW is concluded to be about 37,000 according to the following equation:

$$MW = 193XM = 193X\{151(1-X) + 344X\} \approx 37,000.$$

(3) Determination of the disulfide linkage in the poly-L-glutamate sodium salt-PDM conjugate (DTNB method):

14.8 mg ($4.00 \times 10^{-7}$ moles) of the poly-L-glutamate sodium-PDM conjugate was dissolved in 500 ml of 0.1 M tris.hydrochloric acid-1 mM EDTA solution (pH 8.50). 50 μl of an aqueous solution of 0.1 M dithiothreitol was added thereto and the mixture was made to react at 50° C. for 2 hours (in which the disulfide linkage is cleaved to become —SH group). Thereafter, 50 μl of 0.25 M acetone solution of 5,5'-dithio-bis(2-nitrobenzoic acid) was added to the reaction solution to effect the reaction (to convert the —SH group into the —STNB group). Then the reaction mixture was eluted by Sephadex G-50 (fine) column chromatography over 0.1 M phosphoric acid buffer-1 mM EDTA solution (pH 6.90) to obtain only the polymer by eliminating low molecular compounds. Dithiothreitol was added to the obtained polymer solution to liberate the TNB anions from the terminal —STNB group of the polymer (the polymer again had the SH group at its terminal). The absorbance (412 nm) of the liberated TNB anions in thus obtained polymer solution was measured, from which the concentration of the TNB anions was calculated to be $5.98 \times 10^{-7}$ according to equation (a) of the preceding (2) (in equation (a), $l = 1.0$ cm and $\epsilon = 1.36 \times 10^4$ (absorbancy index of the TNB anions)). The number of moles of the liberated TNB anions is equal to the number of moles of the terminal —STNB groups contained in the polymer, or is twice the number of moles of the polymer having the disulfide linkage. The percentage of the disulfide linkage contained in the poly-L-glutamate sodium-PDM conjugate ($4.00 \times 10^{-7}$ moles) is calculated to be $$\frac{5.98 \times 10^{-7}}{4.00 \times 10^{-7}} \times \frac{1}{2} \times 100 = 74.8\%.$$

From the above fact, it is made clear that about 25% of them do not contain the disulfide linkage in the molecule.

(4) Preparation of the terminal SH group containing poly-L-glutamate-PDM conjugate:

181.1 mg ($4.89 \times 10^{-6}$ moles) of poly-L-glutamate sodium-PDM conjugate (percentage of PDM bond, 21.2%) was dissolved in 6.0 ml of 0.1 M tris.hydrochloric acid-1 mM EDTA solution (pH 8.48), to which 2.0 ml of 0.1 M tris.hydrochloric acid-1 mM EDTA solution (pH 8.45) containing 0.02 M dithiothreitol was added. The mixture was made to react in a tightly sealed reaction system at 50° C. for 100 minutes. (In this reaction, the disulfide linkage in the molecule was cleaved reductively to form two molecules of polymer having the SH group at the terminal of the molecule.)

Then a dispersion prepared by dispersing 8.0 g (dry weight) of an activated thiopropyl sepharose 6B resin (manufactured by Pharmacia, having an

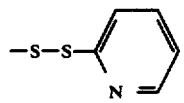

group as a functional group in the resin) in 100 ml of 0.25 M sodium phosphate buffer (pH 6.86) was added to the reaction mixture, which was then kept stirring overnight to allow the resin to adsorb the polymer having an SH group at the terminal of the molecule. (The polymer is adsorbed by the resin to form the resin —S—S—polymer.) Thereafter, the resin which had adsorbed the polymer was filtrated off and washed thoroughly with 800 ml of 0.25 M sodium phosphate buffer (pH 6.86). (The by-product in the reaction of the present invention which was not adsorbed by the resin, or one that has no SH group in the molecule, was removed during this operation.) The washed resin was dispersed in 30 ml of 0.1 M tris.hydrochloric acid-1 mM EDTA solution (pH 8.5), to which dispersion liquid 62 mg of dithiothreitol was added. The reaction system was sealed and stirred overnight to have the polymer regenerated. (During this operation, the polymer adsorbed by the resin was desorbed from the resin and regenerated as a polymer having the SH group at the terminal of the molecule.) The resin was then filtrated off and washed with 400 ml of 0.25 M sodium phosphate buffer (pH 6.86). The filtrate and the washings were put together and, when the pH was adjusted to 4 by adding hydrochloric acid, a polymer having the SH group at the terminal of the molecule was precipitated. The precipitate was collected by centrifugation and dispersed in 6.2 ml of 0.1 M sodium acetate-1 mM EDTA solution (pH 3.96). After argon was bubbled into the dispersion liquid the container was sealed and stored while being cooled (4° C.). The molar volume of thus obtained polymer having the SH group at the terminal of the molecule was $4.86 \times 10^{-6}$ moles when calculated from the end group determination according to the DTNB method. The quantity of the PDM residue measured by use of $\epsilon 275 = 1.62 \times 10^{-4}$ of the acetylated PDM was $108.4 \times 10^{-6}$ moles. Therefore, the present conjugate contains 1 terminal SH group and an average of 22.3(108.4/4.86) PDM residue in a molecule. Since the total number of L-glutamate in the present conjugate is 22.3/0.212 = 105, its molecular weight is calculated to be $105(0.212 \times 344 + 0.788 \times 151) \approx 20,000$.

EXAMPLE 16

This example gives an instance of method to manufacture a polymer having the active disulfide linkage at the terminal (terminal S-TNB-poly-L-glutamate sodium-PDM conjugate).

148 mg of poly-L-glutamate sodium-PDM conjugate obtained in Example 15, (1) was dissolved in 4.0 ml of 0.1 M tris.hydrochloric acid-1 mM EDTA solution (pH 8.5), to which 2.0 ml of 0.1 M tris.hydrochloric acid-1 mM EDTA solution containing 0.02 M dithiothreitol was added in a stream of argon, and the mixed solution was made to react at 40° C. for 3 hours.

A dispersion prepared by dispersing 20 ml (wet volume) of activated thiopropyl sepharose 6B resin in 40 ml of 0.1 M sodium phosphate buffer-1 mM EDTA solution (pH 7.0) was added to the reaction mixture. Argon was passed through the reaction system to displace the air and the reaction mixture was stirred overnight to allow the polymer having the SH group at the terminal of the molecule to be adsorbed by the resin. After that, the resin which had adsorbed the polymer was filtrated off and washed thoroughly with 337 ml of 0.1 M tris.hydrochloric acid-1 mM EDTA solution (pH 8.0). The washed resin was dispersed in 40 ml of 0.1 M tris.hydrochloric acid-1 mM EDTA solution (pH 8.5), to which dispersion liquid 624 mg of 2-mercaptoethanol was added. The mixture was stirred in a stream of argon for 3 hours to regenerate the polymer having the SH group at the terminal of the molecule. The resin was then filtered off and washed with 400 ml of 0.1 M tris.-hydrochloric acid-1 mM EDTA solution (pH 8.5) containing 0.01 M 2-mercapto-ethanol. The filtrate and the washings were put together and the pH value was adjusted to 4 with hydrochloric acid to precipitate the polymer which has the SH group at the terminal of the molecule. After this was left standing at 4° C. for 1 hour, the supernatant was removed by centrifugation. The precipitate was washed with distilled water and a dispersion of the polymer precipitate was obtained. A solution prepared by dissolving 31 mg of 5,5'-dithiobis(2-nitrobenzoic acid) (DTNB) in 30 ml of 1 N sodium phosphate-1 mM EDTA solution (pH 8.0) was added to the dispersion of thus obtained polymer having the SH group at the terminal of the molecule to carry out the reaction while the polymer was being dissolved. After that, the mixed solution was dialyzed against 0.1 N salin solution at 4° C. for 5 days. 50.5 ml of the recovered liquid was subjected to ultrafiltration under reduced pressure with the use of a permeable cellophane membrane until the volume of the liquid was reduced to 1.05 ml. 0.15 ml of 0.1 M sodium phosphate-1 mM EDTA solution (pH 7.0) was added thereto to obtain 1.2 ml of 0.01 M sodium phosphate-0.1 mM EDTA solution (pH 7.0) of the terminal S-TNB-poly-L-glutamate sodium salt-PDM conjugate.

The volume of thus obtained polymer having the —STNB group at the terminal of the molecule was $1.85 \times 10^{-6}$ moles by determination of end group according to the DTNB method. The content of the PDM residue was $53.47 \times 10^{-6}$ moles when measured on the basis of $\epsilon^{275\ nm} = 1.62 \times 10^4$ of acetylated PDM. Therefore, the present conjugate contains 1 terminal —STNB group and an average of 28.9 PDM residue in a molecule. The average molecular weight of this conjugate was calculated to be about 26,000.

EXAMPLE 17

(1) Preparation of poly-L-glutamate sodium salt-daunomycin conjugate:

44.7 mg of the polymer obtained in Example 1, (2) mainly comprising sodium salt of poly-L-glutamic acid was dissolved in 5 ml of water and further 84.4 mg of 1-ethyl-3(3-dimethylaminopropyl) carbodiimide hydrochloric acid salt (EDC) was dissolved therein. An aqueous solution prepared by dissolving 25 mg of daunomycin hydrochloric acid salt in 10 ml of water was added to thus obtained aqueous solution and the mixture was stirred at room temperature for 1 hour. After that, the reaction solution was dialyzed against 0.9% saline solution at 4° C. for 3 days with the use of a permeable cellophane membrane. By adding 1.22 ml of 1.0 M tris.-hydrochloric acid-1 mM EDTA solution (pH 8.5) to 11.0 ml of the recovered liquid, 12.22 ml of 0.1 M tris.-hydrochloric acid-0.1 mM EDTA solution (pH 8.5) of poly-L-glutamate sodium salt-daunomycin conjugate was obtained.

The content of L-glutamate-daunomycin units in the poly-L-glutamate sodium-daunomycin conjugate obtained in the above was $25.6\mu$ moles when determined from the measurement of the absorption (485 nm) of N-acylate product of daunomycin according to the same method as Example 15, (2) (based on $\epsilon = 12,000$).

(2) Preparation of terminal S-TNB-poly-L-glutamate sodium-daunomycin conjugate 1.15 ml of 0.1 M tris.hydrochloric acid-1 mM EDTA solution (pH 8.5) containing 0.02 M dithiothreitol was added to 12.20 ml of 0.1 M tris.hydrochloric acid-0.1 mM EDTA solution (pH 8.5) of poly-L-glutamate sodium-daunomycin conjugate obtained in the preceding (1). The mixture was heated up to 45° C. for 1 hour in an atmosphere of argon and was then left stand at room temperature overnight. A dispersion liquid prepared by dispersing 3.83 g of activated thiopropyl sepharose 6B resin in 40 mL of 0.25 M sodium phosphate-1 mM EDTA solution (pH 6.85) was added to the above mixture and stirred slowly in an atmosphere of argon for 26 hours. Then the resin was separated by filtration and washed with 0.05 M tris.hydrochloric acid-0.5 mM EDTA solution (pH 8.0).

The washed resin was dispersed in 40 ml of 0.1 M tris.hydrochloric acid-1 mM EDTA solution (pH 8.5), to which 359 mg of 2-mercaptoethanol was added. The mixture thus prepared was stirred slowly in an atmosphere of argon for 15 hours. When the reaction was completed, the resin was filtrated off and washed with 50 ml of 0.05 M tris.hydrochloric acid-0.5 mM EDTA solution (pH 8.0) containing 10 mM 2-mercaptoethanol. The mixture of the filtrate and washings had its pH adjusted to 4.0 with hydrochloric acid and was cooled to develop a precipitate (terminal SH-poly-L-glutamate sodium-daunomycin conjugate).

The precipitate was collected centrifugally, washed with water three times, and dissolved in a solution obtained by dissolving 11.64 mg of 5,5'-dithio-bis(2-nitrobenzoic acid) (DTNB) in 5 ml of 1 N-sodium phosphate-1 mM EDTA solution (pH 8.0) convert the terminal SH group into an activated disulfide group (terminal S-TNB group). With the object of purifying thus formed terminal S-TNB-poly-L-glutamate sodium-daunomycin conjugate, the above reaction mixture was fractionated into thirty fractions of 3.93 ml each by chromatography on a column of Sephadex G-25 (fine) equilibrated with 0.05 N sodium phosphate-0.5 mM EDTA solution (pH 6.90). Fractions containing terminal S-TNB-poly-L-glutamate sodium-daunomycin conjugate were detected by measuring the absorption (485 nm) of N-acylated product of daunomycin and the increase of absorbance at 412 nm resulting from the addition of dithiothreitol (absorption of

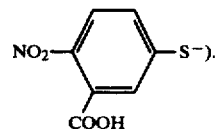

The total of such fractions was concentrated to 4.90 ml under reduced pressure.

The content of the daunomycin residue contained in thus obtained solution was $4.98\mu$ moles when measured on the basis of $\epsilon 485\ nm = 12,000$ of the N-acylated daunomycin and the content of the terminal S-TNB group was $0.538\mu$ mole based on the measurement according to the DTNB method. Therefore, the obtained terminal S-TNB-poly-L-glutamate sodium-daunomycin conjugate has 9.26 daunomycin residues on an average and one S-TNB end group in a molecule.

EXAMPLE 18

This example affords an illustrative instance of a method for preparing a conjugate having an SH group at the terminal of the molecule; the terminal SH-poly-L-glutamate-daunomycin.

7.8 ml of poly-L-glutamate sodium-daunomycin conjugate obtained in example 17 was dissolved in 31.2 ml of 0.1 M tris-hydrochloric acid-1 mM EDTA solution (pH 8.5) to make a total of 39 ml, to which 9.4 mg of dithiothreitol was added and the mixture was left standing overnight to carry out the reaction. After that, the pH of the reaction solution was adjusted to 4.0 by addition of hydrochloric acid and the solution was cooled to develop a precipitate. The precipitate was collected by centrifugation and washed three times with water. The precipitate of polymer thus obtained was dissolved in a dispersion prepared by dispersing 3.0 ml (wet volume) of activated thiopropyl sepharose 6B resin in 10 ml of 0.1 M sodium phosphate-1 mM EDTA solution (pH 8.0). The mixture was stirred slowly overnight to make the resin adsorb the polymer. Thereafter, the resin was filtrated off and washed with 50 ml of 0.05 M tris.hydrochloric acid-0.5 mM EDTA solution (pH 8.0).

The resin was then dispersed in 9 ml of 0.1 M tris.hydrochloric acid-1 mM EDTA solution (pH 8.5), to which 359 mg of 2-mercaptoethanol was added. The mixture was stirred slowly in an atmosphere of argon for 6 hours and a half. After the reaction was over, the resin was collected by filtration and washed with 30 ml of 0.05 M tris.hydrochloric acid-0.5 mM EDTA solution (pH 8.0). The combined solution of the filtrate and the washings had its pH value adjusted to 4.0 with hydrochloric acid, and was cooled to form a precipitate (terminal SH-poly-L-glutamate sodium-daunomycin conjugate).

The obtained precipitate was separated by centrifugation, washed 3 times with water, and 0.1 M sodium acetate—1 mM EDTA solution (pH 4.0) was added thereto to make 2.0 ml of dispersion. The dispersion was stored at 4° C.

The content of the —SH contained in thus obtained terminal SH-poly-L-glutamate sodium-daunomycin conjugate was 0.67μ mole (determined by the DTNB method). The content of bonded daunomycin was 6.0μ moles (based on ε485 nm=12,000 of N-acylated). Therefore, this conjugate contains one terminal SH group and 9 daunomycin residues on an average in a molecule.

EXAMPLE 19

(1) Preparation of poly-L-glutamate sodium-1-(β-D-arabinofranosyl) cytosine (Ara-C) conjugate 210 mg of sodium poly-L-glutamate prepared in Example 2 by use of the initiator n-propyl 2-aminoethyldisulfide was dissolved in 2.0 ml of water and the pH of the solution was adjusted to 3.80 with diluted hydrochloric acid (under cooling) on an ice bath. The precipitate formed was collected by filtration, washed with dilute hydrochloric acid and distilled water, and vacuum dried to give 164 mg of poly-L-glutamic acid as white solid.

64.5 mg (4.5μ moles) of thus obtained poly-L-glutamic acid (average molecular weight, 14,200) was dissolved in 10 ml of anhydrous dimethylformamide. 69 mg of isobutyl chloroformate and 51 mg of triethylamine were added thereto at −8° C. The mixture was stirred for 1 hour to convert the carboxyl groups of poly-L-glutamic acid into mixed acid anhydride. A solution prepared by dissolving 122 mg of Ara-C in 10 ml of anhydrous dimethylformamide and 51 mg of triethylamine were added to the above reaction solution. The mixture was then allowed to go through the reaction in an atmosphere of nitrogen at −8° C. for 30 minutes, at 0° C. for 4 hours, at 4° C. for 3 days, and at 70° C. for 4 hours in this order to conjugate Ara-C to poly-L-glutamic acid. After the reaction was over, the reaction solution was added to 30 ml of 1 M-sodium phosphate buffer (pH 8.0). Thus prepared solution was dialyzed on a cellophane membrane at 4° C. against 0.9% saline solution for 2 days and against pure water for 2 days. About 50 ml of thus obtained solution had its water removed at room temperature under reduced pressure by distillation to reduce the volume to 10 ml.

The ultraviolet absorption spectrum of the obtained solution showed the maximal absorption at 299 nm, 247 nm, and 216 nm and it was understood that $N^4$ position (amino group) of Ara-C formed the amido linkage with the carboxyl group of poly-L-glutamic acid (Refer to M. Akiyama et al., Chem. Pharm. Bull., Vol. 26, p. 981, 1978). The content of Ara-C residue existing in the solution was 0.178 m mole when it was calculated by substituting 1.42, the found value of the absorbance (at 299 nm) in the following equation $$C = A/\epsilon l$$

wherein A is a found value of the absorbance, l is 1.0 cm, and ε indicates the absorbance index (at 299 nm) of $N^4$ position of Ara-C, here being 8,000 for convenience sake.

(2) Preparation of terminal SH-poly-L-glutamate-Ara-C conjugate 2.8 ml of the solution of poly-L-glutamate sodium-Ara-C conjugate obtained in the preceding (1) was mixed with 17.2 ml of 0.1 M tris.hydrochloric acid-1 mM EDTA solution (pH 8.5) to make a total of 20 ml. 7.7 mg of dithiothreitol was added thereto and the reaction was conducted at 45° C. for 3 hours to form the terminal SH group by cleaving the disulfide linkage contained in the polymer. Then the reaction solution had its pH adjusted to 3.8 with hydrochloric acid to let the polymer precipitate. The precipitate was centrifuged and washed with dilute hydrochloric acid. The precipitate of the polymer thus obtained was dissolved in 10 ml of dispersion prepared by dispersing 3.0 ml (wet volume) of activated thiopropyl sepharose 6B resin in 7 ml of 0.1 M sodium phosphate-1 mM EDTA solution (pH 7.8), and the solution was stirred slowly in an atmosphere of argon at 4° C. for 5 hours to make the resin adsorb the polymer having the terminal SH group. After that, the resin was filtrated off and washed with 50 ml of 0.05 M tris.hydrochloric acid-0.5 mM EDTA solution (pH 8.0). The resin was then dispersed in 10 ml of 0.1 M tris.hydrochloric acid-1 mM EDTA solution (pH 8.0) and 92.4 mg of dithiothreitol was added thereto. The mixture was slowly stirred in an atmosphere of argon at 4° C. for 5 hours to have the terminal SH group regenerated. The resin was separated by filtration and washed with 30 ml of 0.05 M tris.hydrochloric acid-0.5 mM EDTA solution (pH 8.0). Hydrochloric acid was added to adjust the pH of the mixture consisting of the filtrate and the washings to 4.0 and a precipitate (terminal SH-poly-L-glutamic acid-Ara-C conjugate) was obtained by cooling the mixture. The precipitate was separated by centrifugation, washed with dilute hydrochloric acid three times, dispersed in 0.1 M sodium acetate buffer-1 mM EDTA solution (pH 3.5) to make 2.0 ml of dispersion, and stored at 4° C.

The content of —SH contained in the terminal SH-poly-L-glutamate-Ara-C bond thus obtained was determined as 0.63μ mole by the DTNB method. The content of the bound Ara-C measured and calculated on the basis of ε299 nm=8,000 of the $^4N$ acylated Ara-C was 13.5μ moles. This conjugate accordingly has 1 terminal SH group and 21.4 Ara-C residues on an average in one molecule.

EXAMPLE 20

(1) Preparation of L-glutamate/L alanine copolymer sodium salt-melphalan conjugate 450 mg of the polymer mainly comprising sodium of L-glutamate/L-alanine copolymer obtained in Example 3 was dissolved in 10 ml of water, to which an aqueous solution prepared by dissolving 66.3 mg of 1-ethyl-3-(3-dimethylaminopropyl) carbodiimide hydrochloride (EDC, condensing agent) in 5 ml of water was added. An aqueous solution prepared by dissolving 88.5 mg of P-[bis(2-chloroethyl)amino]L-phenylalanine (melphalan), which is a publicly known anti-cancer drug, in 20 ml of water was added dropwise to the mixed solution in 10 minutes. This reaction solution was stirred overnight at room temperature. When hydrochloric acid was added to the reaction solution to adjust the pH to 4.0, a white precipitate appeared. The precipitate was isolated by centrifugation and was washed with dilute hydrochloric acid. Thus obtained white solid was dissolved in 20 ml of 0.1 N caustic soda solution and dialyzed against pure water at 4° C. for 3 days on a permeable cellophane tube. The dialyzate was lyophilized to give 484 mg of L-glutamic acid/L-alanine copolymer sodium salt-melphalan conjugate as a curdy solid.

The ultraviolet absorption spectrum of the aqueous solution of the obtained product showing the maximal absorption at 258.5 nm and 302.0 nm proved that the primary amino group of melphalan formed amide linkage with the carboxyl group of L-glutamic acid residue contained in the copolymer to link to the polymer. The quantity of melphalan contained in 484 mg of the said curdy solid was $0.263\mu$ mole when measured on the assumption that the molecular absorbancy index of melphalan coupled with the polymer was equal to that of free melphalan ($\epsilon 258.5$ nm=$1.37 \times 10^4$) for convenience sake.

(2) Preparation of terminal SH-poly-L-glutamate-L-alanine-melphalan conjugate 400 mg of solid poly-L-glutamate-L-alanine-melphalan conjugate obtained in the preceding (1) was dissolved in 15 ml of 0.1 M tris.hydrochloric acid-1 mM EDTA solution (pH 8.5), to which 12.8 mg of dithiothreitol was added. The reaction was carried out in a sealed system at 45° C. for 3 hours, during which time the disulfide linkage in the polymer was cleaved and the terminal SH group was generated. The pH of the reaction solution was adjusted to 3.4 with 1 N hydrochloric acid to make the polymer precipitate. The precipitate was isolated by centrifugation and washed with diluted hydrochloric acid three times. The precipitate of the polymer thus obtained was dissolved in 30 ml of 0.1 N NaOH solution. The prepared solution was added to a dispersion obtained by dispersing 46 ml (wet volume) of activated thiopropyl sepharose 6B resin in 50 ml of 0.1 M sodium phosphate-1 mM EDTA solution (pH 7.5). The mixture was stirred slowly in an atmosphere of nitrogen at room temperature to allow the resin to adsorb the polymer having the terminal SH group. The resin was filtrated off and washed with 1000 ml of 0.1 M tris.hydrochloric acid-1 mM EDTA solution (pH 8.0). Then the resin was dispersed in 70 ml of 0.1 M tris.hydrochloric acid-1 mM EDTA solution (pH 8.5), and after 770 mg of dithithreitol was added thereto, the mixture was stirred slowly overnight in an atmosphere of nitrogen to have the terminal Sh group regenerated. The resin was separated by filtration and washed with 300 ml of 0.05 M tris.hydrochloric acid-0.5 mM EDTA solution (pH 8.5). 1 N hydrochloric acid was added to the mixture of the filtrate and the washings to adjust the pH to 3.5 and the solution was cooled to precipitate the terminal SH-poly-L-glutamate-L-alanine-malphalan conjugate. The precipitate was isolated by centrifugation, washed with dilute hydrochloric acid three times, dispersed in 10 ml of 0.1 M sodium acetate buffer-1 mM EDTA solution (pH 3.0), and stored at 4° C.

The content of the —SH group contained in the terminal SH-poly-L-glutamate-L-alanine-melphalan conjugate thus obtained was $9.1 \times 10^{-6}$ mole according to the DTNB method. The content of melphalan bound to the polymer was $92.1 \times 10^{-6}$ mole when measured and calculated based on $\epsilon 258.5$ nm=$1.37 \times 10^4$. Therefore, this conjugate contains one terminal SH group and 10.1 melphalan residue on an average in one molecule.

What is claimed is:

1. A reactive polymer having a degree of polymerization in the range of 5 to 3,000, with 60 mole % or more of all of the constituent units of the polymer comprising constituent units expressed by formula (I)

wherein Z represents a hydrogen atom or a univalent cation; m is an integer of 1 to 4;

and having an active group expressed by formula (II) at the —CO— moiety of the unit expressed by formula (I) at a terminal of the main chain containing units expressed by formula (I)

wherein X represents a hydrogen atom or a group which forms an active disulfide linkage together with a neighboring sulfur atom; W is an inert divalent organic group; and $R_1$ represents a hydrogen atom or an alkyl group having 1 to 4 carbon atoms.

2. A reactive polymer according to claim 1, wherein W in the formula (II) is an alkylene group having 1 to 4 carbon atoms.

3. A reactive polymer according to claim 1, wherein X in the formula (II) is a group, which forms an active disulfide linkage, selected from the group consisting of a 2-pyridylthio group, a 4-pyridylthio group, a 3-carboxy-4-nitrophenylthio group, a 4-carboxy-2-pyridylthio group, an N-oxy-2-pyridylthio group, a 2-nitrophenylthio group, a 4-nitro-2-pyridylthio group, a 2-benzothiazolylthio group, a 2-benzoimidazolylthio group and an N-phenylamino-N'-phenyliminomethylthio group.

4. A hydrophilic polymer having a degree of polymerization in the range of 5 to 3,000, with 60 mole % or more of all of the constituent units of the polymer comprising constituent units expressed by formula (I)

wherein Z represents a hydrogen atom or a univalent cation; m is an integer of 1 to 4; and having a disulfide linkage-containing group expressed by formula (III) in the main chain or at the —CO— moiety of the unit expressed by formula (I) at a terminal of the main chain containing units expressed by formula (I)

wherein W is an inert divalent organic group; $R_1$ represents a hydrogen atom or an alkyl group having 1 to 4 carbon atoms; and $R_2$ represents an alkyl group, an aralkyl group or an aryl group, when the group expressed by formula (III) is a terminal group of the main chain containing units expressed by formula (I), and represents a divalent group represented by

when the group expressed by formula (III) is in the main chain containing units expressed by formula (I), where W' is a divalent organic group identical with or different from W and is linked with S of formula (II); $R_1'$ is identical with or different from $R_1$ and represents a hydrogen atom or an alkyl group having 1 to 4 carbon atoms.

* * * * *